（12） United States Patent
Souno et al.

(10) Patent No.: US 8,568,986 B2
(45) Date of Patent: Oct. 29, 2013

(54) METHOD OF SELECTING AN AGENT THAT IMPROVES PERIODONTAL DISEASE

(75) Inventors: Hatsumi Souno, Haga-gun (JP);
Hidetake Fujinaka, Haga-gun (JP);
Junji Nakamura, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/529,717

(22) Filed: Jun. 21, 2012

(65) Prior Publication Data

US 2012/0276546 A1 Nov. 1, 2012

Related U.S. Application Data

(62) Division of application No. 13/258,700, filed as application No. PCT/JP2010/056778 on Apr. 15, 2010, now Pat. No. 8,293,478.

(30) Foreign Application Priority Data

Apr. 24, 2009 (JP) ................................ 2009-107085

(51) Int. Cl.
*C12Q 1/68* (2006.01)
(52) U.S. Cl.
USPC ........................................ 435/6.15; 435/6.13
(58) Field of Classification Search
None
See application file for complete search history.

(56) References Cited

U.S. PATENT DOCUMENTS

| | | | | |
|---|---|---|---|---|
| 6,726,898 | B2 * | 4/2004 | Jernberg | 424/49 |
| 7,427,408 | B2 | 9/2008 | Merritt et al. | |
| 2006/0269998 | A1 * | 11/2006 | Buck et al. | 435/69.1 |
| 2007/0172434 | A1 * | 7/2007 | Jernberg et al. | 424/49 |
| 2009/0269323 | A1 * | 10/2009 | Luk et al. | 424/94.3 |

FOREIGN PATENT DOCUMENTS

| | | |
|---|---|---|
| EP | 1 640 721 A1 | 3/2006 |
| JP | 10-002899 A | 1/1998 |
| JP | 2000-028608 A | 1/2000 |
| JP | 2008-214296 A | 9/2008 |
| WO | WO 02/47681 A1 | 6/2002 |
| WO | WO 2004/055202 A2 | 7/2004 |
| WO | WO 2009/029317 A2 | 3/2009 |

OTHER PUBLICATIONS

Rasmussen TB, et al. Microbiology 152:895-904, 2006.*
International Search Report (ISR) for PCT/JP2010/056778, I.A. fd: Apr. 15, 2010, mailed Jul. 27, 2010 from the Japanese Patent Office, Tokyo, Japan.
International Preliminary Report on Patentability (IPRP), Chapter I of the Patent Cooperation Treaty, including the Written Opinion for PCT/JP2010/056778, I.A. fd: Apr. 15, 2010, issued Nov. 22, 2011, from the International Bureau of WIPO, Geneva, Switzerland.
Azakami, H. et al., "Purification and characterization of autoinducer-2 of periodontopathogenic bacterium, *Eikenella corrodens*," Abstract 2Ha08, in a collection of the 60$^{th}$ meeting of the Society for Bioscience and Bioengineering, Japan, meeting lecture syllabus, Jul. 11, 2008, p. 196.
Azakami, H, et al., "Development of new therapies of periodontal diseases targeted for quorum sensing," ("Kiso Kenkyu no Aratana Hokosei o Toku 40) Shikkan Kaimei Overview Quorum Sensing o Target to shita Shishubyo Chiryoho no Kaihatsu"), Experimental Medicine 26(6): 945-949 (Apr. 2008), Medical Online, Japan.
Turovskiy, Y, et al., "Autoinducer-2 bioassay is a qualitative, not quantitative method influenced by glucose," J Microbiol Methods 66(3):497-503 (Sep. 2006), Elsevier, Amsterdam, The Netherlands.
Okuda, K., "New challenge on intraoral biofilm infectious disease," ("Kokunai Bio Film Kansensho eno Aratana Chosen"), Dental Outlook 99(5): 1061-1068 (2002), Ishiyoku Shuppan, K.K., Tokyo, Japan.
Ito, K., "The importance of establishing a clinical examination system for periodontal disease: How to proceed? Effectiveness of novel clinical examination systems for periodontal disease using saliva sample," Japan Dental Assoc. Medicine Bull. 24: 112-115 (2005), Japan Dental Assoc., Tokyo, Japan.
Yoshida, A, "LuxS-Based Signaling Affects *Streptococcus mutans* Biofilm Formation," Appl. Envir. Microbiol. 71: 2372-2380 (May 2005), Am. Soc. Microbiology, Washington, DC.
Wen, ZT et al., "LuxS-Mediated Signaling in *Streptococcus mutans* Is Involved in Regulation of Acid and Oxidative Stress Tolerance and Biofilm Formation," J. Bacteriol.186: 2682-2691 (May 2004), Am. Soc. Microbiology, Washington, DC.
Schauder S. et al., "The LuxS family of bacterial autoinducers: biosynthesis of a novel quorum-sensing signal molecule," Molecular Microbiology 41(2), 463-476 (2001), Blackwell Science Ltd.
Cao, J-G., and Meighen, E.A., "Purification and Structural Identification of an Autoinducer for the Luminescence System of *Vibrio harueyi*," The Journal of Biological Chemistry 246(36):21670-21676; The American Society for Biochemistry and Molecular Biology, Inc., United States (1989).
Frias, J., et al., "Periodontal Pathogens Produce Quorum Sensing Signal Molecules," *Infection and Immunity* 69(5):3431-3434, American Society for Microbiology, United States (2001).
Azakami, H., et al., "Characterization of Autoinducer 2 Signal in *Eikenella corrodens* and Its Role in Biofilm Formation," *Journal of Bioscience and Bioengineering* 102(2):110-117, The Society for Biotechnology, Japan (2006).
Supplementary European Search Report for EP Application No. 10767003, Hague, Netherlands, dated Sep. 5, 2012.
Partial European Search Report for EP Application No. 13 16 3479, Hague, Netherlands, mailed Jul. 30, 2013.

* cited by examiner

*Primary Examiner* — Robert Landsman
(74) *Attorney, Agent, or Firm* — Sterne, Kessler, Goldstein & Fox P.L.L.C.

(57) ABSTRACT

A marker for determining the onset of periodontal disease and a marker far determining the progression stage of periodontal disease, each containing autoinducer-2.

9 Claims, 1 Drawing Sheet

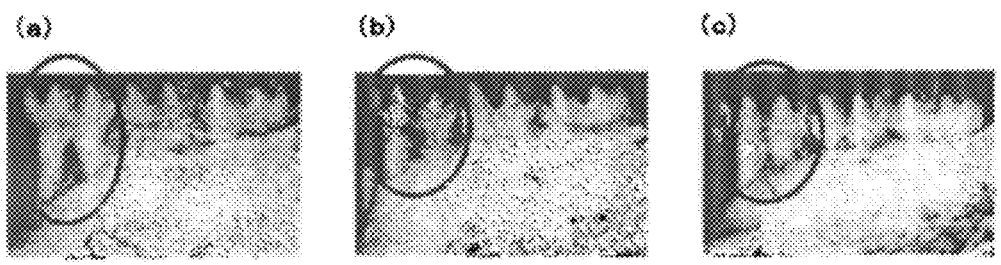

METHOD OF SELECTING AN AGENT THAT IMPROVES PERIODONTAL DISEASE

TECHNICAL FIELD

The present invention relates to a periodontal disease marker.

BACKGROUND ART

A periodontium is a tissue which is present around teeth and plays a role in supporting teeth. It is composed of a gum, periodontal membrane, cementum, and alveolar bone. Among the periodontium inflammations, an inflammation confined to the gum is referred to as "gingivitis", while the case where inflammation sites extend beyond the gum, and the periodontal membrane and/or alveolar bone are damaged and broken is referred to as "periodontitis". A general term of these inflammations is "periodontal disease".

The periodontal disease such as gingivitis and periodontitis is endogenous infectious disease caused by an increase in bacteria in a dental plaque (a lump propagated by attachment of bacteria to food residues in the oral cavity), an influence of other factors, and an inflammation of periodontium. The periodontal disease is different from dental caries, and it causes little pain and progresses before while being noticed in many cases. However, leaving the periodontal disease untreated results in progression of symptoms and there is a high possibility that teeth are eventually lost. An increase in the risk of cardiovascular disease is also another concern.

Periodontal disease strategies include preventive behaviors such as right toothbrushing, plaque control in regular checkups, and improvement in eating habits. However, realistically, it is very important how to discover ongoing periodontal disease by periodontal disease diagnosis and perform a suitable treatment for the symptom.

Diagnosis of periodontal disease is generally performed by measurement of a periodontal pocket, attachment level, X-ray image diagnosis, or the like. However, these diagnosis methods increase the burden of subjects. Further, these methods for diagnosing periodontal disease have a complicated operating procedure and there is a problem such that the determination standard varies with dentist's individual experiences or skills.

As a method of diagnosing periodontal disease using a periodontal disease marker, a method of diagnosing periodontal disease containing: collecting a gingival crevice fluid with a brush-shaped instrument for collecting it; and detecting biomarkers such as lactoferrin, α1-antitrypsin, and hemoglobin contained in the gingival crevice fluid is known (for example, referred to Patent Literatures 1 and 2). However, components other than a gingival crevice fluid are also contained in the gingival crevice fluid and thus it lacks accuracy when saliva is mixed therein. Further, a method of diagnosing periodontal disease containing detecting occult blood (hemoglobin) in saliva or a spat mouthwash is known (for example, refer to Non-Patent Literature 1). However, components other than the component derived from periodontal disease may also be mixed in occult blood in saliva. Further, the amount of saliva varies among different individuals and exhibits high daily variation and there is no quantitative performance of hemoglobin, thereby being impossible to diagnose the progression stage of periodontal disease.

CITATION LIST

Patent Literatures

Patent Literature 1: JP-A-10-2899 ("JP-A" means unexamined published Japanese patent application)
Patent Literature 2: JP-A-2000-28608
Non-Patent Literature 1: Koichi Ito, Journal of the Japanese Association for Dental Science, 24, p. 112-115, 2005

SUMMARY OF INVENTION

Technical Problem

An object of the present invention is to provide a marker for determining the onset of periodontal disease which can simply and accurately determine the presence or absence of the onset of periodontal disease.

Another object of the present invention is to provide a marker for determining the progression stage of periodontal disease which can simply and accurately determine the degree of progression of periodontal disease.

Still another object of the present invention is to provide a method of determining the onset of periodontal disease which can simply and accurately determine the presence or absence of the onset of periodontal disease.

Still another object of the present invention is to provide a method of determining the progression stage of periodontal disease which can simply and accurately determine the degree of progression of periodontal disease.

Still another object of the present invention is to provide a method of screening an improving agent or preventive agent for periodontosis which is effective in accurately and simply screening an improving agent or preventive agent for periodontosis which is effective for prevention and improvement of periodontal disease.

Solution to Problem

Bacteria have acquired a mechanism for acutely sensing changes of the growth environments. It has been clarified that, as one of such mechanisms, microorganisms sense their concentrations in the environments via specific signaling substances and cleverly control a variety of their bioactivities depending on the concentrations. Such intercellular signaling mechanism is referred to as a quorum sensing system.

A bacterium having a quorum sensing system synthesizes and releases a signaling molecule, called an autoinducer, and controls gene expression as a function of cell density in response to the signaling molecule. There has been a report that autoinducer-2 is used for communication between different bacterial species (see, for example, Bassler et al., Bacteriol. 179, pp. 4043-4045, 1997).

As oral indigenous bacteria, about 600 kinds of bacteria are present. Among them, the presence of many periodontal pathogens such as *Porphyromonas* bacterium, *Streptococcus* bacterium, *Eikenella* bacterium, *Lactobacillus* bacterium, *Actinobacillus* bacterium, *Actinomyces* bacterium, *Fusobacterium* bacterium, *Veillonella* bacterium, *Capnocytophaga* bacterium, and *Prevotella* bacterium is known. These periodontal pathogens increase, secrete exopolysaccharide, and form biofilms, thereby an increase in pathogenicity and causing the onset of periodontal disease.

In JP-A-2008-214296, a biofilm formation inhibitory effect in the case of adding an antagonist of autoinducer-2 receptor using a *Porphyromonas gingivalis* strain which is one of periodontal pathogens is examined. However, as for the periodontal pathogen, many bacterial species other than *Porphyromonas gingivalis* are present. Further, there is an effect of oral indigenous bacteria other than periodontal pathogens to periodontal pathogen. Consequently, it is impossible to clinically explain the level or severity of periodontal disease in mammals such as humans even if the biofilm formation inhibitory effect is examined using only a *Porphyromonas gingivalis* strain.

The present inventors conducted intensive studies in view of the above problems. As a result, they have revealed an influence of autoinducer-2 in vivo on periodontal disease and found out that there is a correlation between periodontal disease and the amount of autoinducer-2 being used for communication among different kinds of bacteria released when indigenous bacteria in the oral cavity increase. Specifically, they have found that the presence or absence of the onset of periodontal disease and the progression stage of periodontal disease are associated with the amount of autoinducer-2 in the oral cavity. Further, they have found that a substance having an autoinducer-2 activity inhibitory effect is effective in improvement and prevention of periodontal disease. The present invention is completed based on these findings.

The present invention relates to a marker for determining the onset of periodontal disease, containing autoinducer-2.

Further, the present invention relates to a marker for determining the progression stage of periodontal disease, containing autoinducer-2.

Further, the present invention relates to a method of determining the onset of periodontal disease containing: collecting a specimen from an oral cavity of a subject; quantifying autoinducer-2 contained in the collected specimen; and determining that periodontal disease is present when the amount of the quantified autoinducer-2 is large.

Further, the present invention relates to a method of determining the progression stage of periodontal disease, containing: collecting a specimen from an oral cavity of a subject; quantifying autoinducer-2 contained in the collected specimen; and determining that periodontal disease is progressive as the amount of the quantified autoinducer-2 is large.

Further, the present invention relates to a method of screening an improving agent or preventive agent for periodontal disease, containing mixing a bacterium having an autoinducer-2-mediated quorum sensing system with a test drug; and selecting a test drug, having an autoinducer-2 activity inhibitory effect as an improving agent or preventive agent for periodontal disease.

Further, the present invention relates to use of autoinducer-2 as a marker for determining the onset of periodontal disease.

Further, the present invention relates to use of autoinducer-2 as a marker for determining the progression stage of periodontal disease.

Advantageous Effects of Invention

According to the marker for determining the onset of periodontal disease of the present invention, the presence or absence of the onset of periodontal disease can be determined simply and accurately.

According to the marker for determining the progression stage of periodontal disease, the degree of progression of periodontal disease can be determined simply and accurately.

According to the method of determining the onset of periodontal disease of the present invention, the presence or absence of the onset of periodontal disease can be determined simply and accurately.

According to the method of determining the progression stage of periodontal disease of the present invention, the degree of progression of periodontal disease can be determined simply and accurately.

According to the method of screening an improving agent or preventive agent for periodontal disease, the improving agent or preventive agent for periodontosis which is effective for prevention and improvement of periodontal disease can be screened simply and accurately.

Other and further features and advantages of the invention will appear more fully from the following description, appropriately referring to the accompanying drawings.

BRIEF DESCRIPTION OF DRAWINGS

FIGS. 1(*a*) to (*c*) are photographs substituted for drawings obtained by photographing the mandibule extracted after two weeks following administration of a control as a test drug (FIG. 1(*a*)), 4-bromo-5-(4-methoxyphenyl)-2(5H)-furanone (FIG. 1(*b*)), and 3,4-dibromo-5-hydroxy-2(5H)-furanone (FIG. 1(*c*)) to a mandibular first molar of syrian hamster (the circled portion) in Example 2 with a stereoscopic microscope.

MODE FOR CARRYING OUT THE INVENTION

Hereinafter, the present invention is described in detail based on preferred embodiments of the present invention.

The marker for determining the onset of periodontal disease of the present invention (simply also referred to as a marker for determining periodontal disease) and the marker for determining the progression stage of periodontal disease are comprised of autoinducer-2 collected from the oral cavity of subjects such as humans. Autoinducer-2 (hereinafter, also referred to as "AI-2") in the present invention is not particularly limited as long as it is produced by bacteria and has AI-2 activity.

In the present invention, the AI-2 activity is an activity to affect a bacterium having a quorum sensing system, namely, an activity to promote a bacterial function induced by the quorum sensing via AI-2. By the AI-2-mediated quorum sensing, bacteria are known to show photogenesis, swarming, formation of biofilms, production of proteases, synthesis of antibiotics, development of gene-recognizing ability, plasmid conjunctional transfer, production of pathogenic factors, spore formation, and the like. Therefore, the AI-2 activity is, that is to say, an activity of a bacterium which recognizes AI-2, i.e., a bacterium having an AI-2 receptor, to show bioluminescence, swarming, formation of biofilms, production of proteases, synthesis of antibiotics, development of gene-recognizing ability, plasmid splicing transmission, production of pathogenic factors, and spore formation. Examples of the pathogenic factor include, but not limited to, enterotoxin, adenylate cyclase toxin, adhesin, alkaline protease, hemolysin toxin, anthrax toxin, APX toxin, α toxin, β toxin, δ toxin, C2 toxin, C3 toxin, botulinum toxin, submit of bundle forming pilus structure, C5A peptidase, cardiac toxin, chemotaxis, cholera toxin, ciliary body toxin, clostridial cell toxin, clostridial nerve toxin, collagen adhesion gene, cytolysin, emetic toxin, endotoxin, exfoliatin toxin, exotoxin, extracellular elastase, fibrinogen, fibronectin-bonded protein, filamentous hemagglutinin, fimbriae, gelatinase, hemagglutinin, leukotoxin, lipoprotein signal peptidase, listeriolysin O, M protein, nerve toxin, non-fimbriae adhesins, edema factor, permease, pertussis toxin, phospholipase, pilus, pore-forming toxin, proline permease, serine protease, Shiga toxin, tetanus toxin, thiol activation cytolysin, trachea cytolysin, and urease.

Specific examples of the AI-2 in the present invention include 4,5-dihydroxy-2,3-pentanedione (DPD) represented by the formula described below.

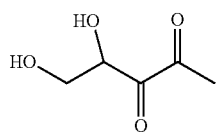

The DPD takes in boron at the time of bounding to an AI-2 receptor of a bacterium and is converted into a furanosyl borate diester. Another specific example of the AI-2 in the present invention includes the furanosyl borate diester.

Specific examples of the furanosyl borate diester above are described below. However, the present invention is not limited thereto.

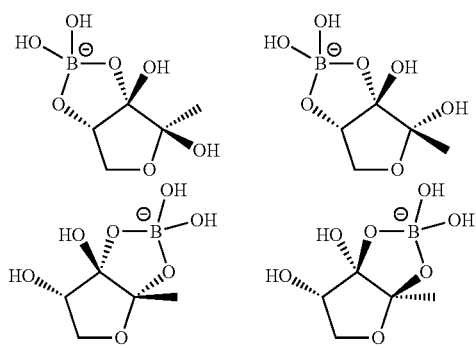

Examples of the bacterium having an AI-2 receptor include *Porphyromonas* bacterium, *Haemophilus* bacterium, *Bacillus* bacterium, *Neisseria* bacterium, *Streptococcus* bacterium, *Eikenella* bacterium, *Lactobacillus* bacterium, *Actinobacillus* bacterium, *Actinomyces* bacterium, *Bacteroides* bacterium, *Capnocytophaga* bacterium, *Fusobacterium* bacterium, *Peptococcus* bacterium, *Prevotella* bacterium, *Selemonas* bacterium, *Eubacterium* bacterium and *Veillonella* bacterium. Specific examples thereof include *Porphyromonas gingivalis*, *Streptococcus pyogenes*, *Streptococcus mutans*, *Eikenella corrodens*, *Lactobacillus salivarius*, *Streptococcus sanguinis*, *Streptococcus anginosus*, *Streptococcus oralis*, *Streptococcus gordonil*, *Streptococcus mitis*, *Actinobacillus actinomycetemcomitans*, *Lactobacillus rhamnosus*, *Actinomyces naeslundii*, *Fusobacterium nucleatum*, *Veillonella parvula*, *Capnocytophaga sputigena* and *Prevotella intermedia*.

In the present invention, AI-2 for use is collected from the oral cavity of a subject such as humans. Here, examples of the subject include mammals such as humans, monkeys, chimpanzees, dogs, cats, cows, pig, rats, and mice. The AI-2 is not particularly limited as long as it is collected from the oral cavity. AI-2 contained in specimens such as saliva collected from the oral cavity, dental plaque, coating of tongue, and gingival crevice fluid can be used. In the present invention, it is preferable to use AI-2 contained in a dental plaque. Saliva can be obtained as one obtained by directly spitting or one obtained by gargling with water regardless of each stimulation or non-stimulation period. The dental plaque can be collected by cleaning of the tooth surface with a dental scaler, swab, brush or the like or insertion of a paper point. The coating of tongue is obtained by cleaning with a brush, swab, gauze, or the like. The gingival crevice fluid can be obtained by inserting a paper point and the like into gingival sulcus. However, a method of collecting AI-2 is not limited thereto.

The present inventors have found that when the amount of AI-2 present in the oral cavity of a subject is large, the subject has periodontal disease. Further, they have found that periodontal disease is progressive as the amount of AI-2 is large. Therefore, the presence or absence of the onset of periodontal disease of a subject and the progression stage (severity) of periodontal disease can be determined by quantifying the amount of AI-2 collected from the oral cavity. As an example, in the case where the AI-2 activity with 10 μM of DPD is defined as 100, when the AI-2 activity is 0 or more and less than 3, it can be determined to be healthy or mild periodontal disease; when the AI-2 activity is 3 or more and less than 10, it can be determined to be moderate periodontal disease; and when the AI-2 activity is 10 or more, it can be determined to be serious periodontal disease. Effects of treatment can be also determined by comparing the amount of AI-2 before initiation of therapy of periodontal disease with the amount of AI-2 after therapy.

A method of quantifying AI-2 is not particularly limited and the quantification can be performed by an ordinary method (see, for example, Chen X. et al., Nature, vol. 415, p. 545-549, 2002; and Thiel V. et al., Chembiochem., vol. 10(3), p. 479-485, 2008).

AI-2 can be quantified by bioassay for measuring the photogenesis intensity using, for example, a reporter bacterium which recognizes AI-2 and emits light (preferably an AI-2 receptor) and a bacterium having luciferase activity. For example, AI-2 can be quantified from the photogenesis intensity when a *Vibrio harveyi* BB170 strain is an AI-2 reporter bacterium, a calibration curve related to 4-hydroxy-5-methyl-3(2H)-furanone (HMF) authentic preparation and/or a DPD authentic preparation is made as a standard sample of AI-2, and a test sample is added (see, for example, Chen X. at al., Nature, vol. 415, p. 545-549, 2002). After the reaction of AI-2 contained in the test sample with phenylenediamine and N-methyl-N-(trimethylsilyl)trifluoro acetamide, AI-2 can be quantified by GC-MS (see, for example, Thiel V. et al., Chembiochem., vol. 10(3), p. 479-485, 2008). However, the present invention is not limited thereto.

As for the test sample for quantifying AI-2, it is preferable that a specimen collected from the oral cavity is crushed/extracted and the resultant product is ultrafiltered through a filter with a molecular weight cut-off of 3000 or less to remove contaminants.

In the present invention, it is preferable that the preparation and storage of the test sample are performed using a container with low adsorptive properties of AI-2, such as a glass container. The use of the glass container allows for accurate quantification of AI-2 contained in the test sample.

The method of screening an improving agent or preventive agent for periodontal disease of the present invention containing mixing a bacterium having an autoinducer-2-mediated quorum sensing system with a test drug and selecting a test drug having an autoinducer-2 activity inhibitory effect as an improving agent or preventive agent for periodontal disease. For example, a *Vibrio harveyi* BB 170 strain is prepared in a culture medium at 1000- to 10000-fold dilution (preferably 4000- to 5000-fold) and preincubated with a test compound solution at room temperature for 1 to 30 minutes (preferably for 10 minutes). Then, AI-2 was added to the resultant solution, which was subjected to aerobic shaking culture at 30±5° C. Two (2) to six (6) hours later (preferably four (4) hours later), the photogenesis intensity is measured with a chemiluminescence analyzer. The final concentration of AI-2 is from 0.001 to 100 µM (preferably 10 µM). The final concentration of the test compound solutions is from 0.0001 to 0.1% or from 1 to 100 µM. Each concentration is not limited thereto. The photogenesis intensity when a control obtained by adding only the AI-2 is mixed with the test compound solution is measured as a relative value to the photogenesis intensity of control so that the AI-2 activity inhibitory effect of the test compound can be measured. The bacterium having an autoinducer-2-mediated quorum sensing system is not particularly limited. A reporter bacterium which recognizes the autoinducer-2 thereby emitting light is preferred and dental bacteria and periodontal pathogens can also be used. Further, the bacterium having an autoinducer-2-mediated quorum sensing system which is collected from the oral cavity of a subject can also be used as a specimen.

The term "autoinducer-2 activity inhibitory effect" herein means an inhibitory effect on the AI-2 activity. Specifically, it indicates inhibitory effect on the AI-2 activity, such as bioluminescence, swarming, biofilm formation, production of proteinase, synthesis of antibiotic substances, development of gene-recipient ability, plasmid conjugational transfer, production of pathogenic factors and sporulation of the bacterium having an AI-2 receptor.

The test drug having an AI-2 activity inhibitory effect selected by the screening method of the present invention can be used as an inhibitor of AI-2 activity or an improving agent or preventive agent for periodontal disease. The inhibitor of AI-2 activity can be suitably used as a material for preparing the improving agent or preventive agent for periodontal disease.

EXAMPLES

Hereinafter, the present invention will be described more in detail with reference to Examples, but the present invention is not limited thereto.

Example 1

Determination of Onset of Periodontal Disease and Progression Stage of Periodontal Disease (1) Quantification of AI-2 in Dental Plaque A *Vibrio harveyi* BB170 strain (purchased from ATCC, cultured in AB (Autoinducer Bioassay) medium (10 mM potassium phosphate buffer [pH7.0]), 0.3 M NaCl, 0.05 M $MgSO_4$, 0.2% casamino acids, 2% glycerol, 1 mM L-arginine, 1 µg/mL thiamin, and 0.01 µg/mL riboflavin) at 30° C. overnight) was used as an AI-2 reporter bacterium and it was 5000-fold diluted with an AB culture medium to prepare a reporter bacterium liquid. An HMF authentic preparation (manufactured by SIGMA) with various concentrations or a DPD authentic preparation (manufactured by OMM Scientific) was mixed with the reporter bacterium liquid at a volume ratio of (reporter bacterium liquid):(authentic preparation)=9:1, followed by culturing with aerobic shaking at 30° C. Four (4) hours later, the photogenesis intensity was measured with the chemiluminescence analyzer (LB940 type, manufactured by Berthold Japan co. ltd.) and a calibration curve related to the photogenesis intensity and the amount of AI-2 was prepared.

Among 94 male and female subjects in their 20s to 90s, subjects in whom samples would be collected in the morning were not allowed to brush their teeth after toothbrushing before bedtime before the test and subjects in whom samples would be collected in the afternoon were not allowed to brush their teeth after toothbrushing on the morning of the test day. Further, they were not allowed to eat, drink, and smoke from 30 minutes before sampling.

The total amount (0.001 to 100 mg) of the subgingival dental plaque attached to the tooth surface of one (1) tooth was collected with the dental scales. The collected dental plaque was dispersed in 1 mL of PBS and incubated at 90° C. for 10 minutes, followed by crushing with 0.3 g of zirconia/silica beads (particle diameter: 0.1 mm, manufactured by TOMY SEIKO CO., LTD.). After centrifugation at 14000 rpm for 5 minutes, a sample was prepared by passing a supernatant through a 0.22-µm filter (Ultra-free MC, manufactured by Millipore) and further passing it through a filter with a molecular weight cut-off of 3000 (Microcon YM-3, manufactured by Millipore). The thus-prepared sample was mixed with the reporter bacterium liquid prepared in the same manner as above at a volume ratio of (reporter bacterium liquid):(sample)=9:1, followed by aerobic shaking culture at 30° C. Four (4) hours later, the photogenesis intensity was measured with the chemiluminescence analyzer. The amount of the AI-2 contained in the dental plaque was quantified from the measured photogenesis intensity and the calibration curve.

(2) Relationship Between Amount of AI-2 in Dental Plaque and Pocket Depth (PD)

A dental probe was inserted into a subject's periodontal pocket, and the pocket depth (PD) was measured and evaluated on a 3-point scale. The pocket depth (PD) was measured for every millimeter.

(PD)

3 mm or less: Healthy or mild periodontal disease (gingivitis)

4-5 mm: Moderate periodontal disease (periodontitis)

6 mm or more: Serious periodontitisperiodontal disease (periodontitis)

A relationship between the PD measured in the above manner and the amount of AI-2 measured in (1) is shown in Table 1.

TABLE 1

| PD | AI-2 amount (average, nmol/one (1) tooth) | SE | Dunnett |
|---|---|---|---|
| 3 mm or less | 0.82 | 0.22 | — |
| 4-5 mm | 2.35 | 0.38 | $P < 0.05$ |
| 6 mm or more | 2.74 | 0.91 | $P < 0.05$ |

As is apparent from Table 1, there is a correlation between the amount of AI-2 in the dental plaque and the PD, and the amount of AI-2 contained in the subgingival dental plaque is increased as the PD becomes deeper. Therefore, the presence or absence of the progression stage of periodontal disease can be determined simply and accurately by quantifying the amount of AI-2 in a subject's oral cavity.

(3) Relationship Between Amount of AI-2 in Dental Plaque and Gingival Index (GI)

A dental probe was inserted into a subject's periodontal pocket, and the level of inflamed gum was evaluated on a 4-point scale. Gingival Index (GI) score evaluation is as follows:

(GI)

0: Normal gum

1: Inflammation in the gum. No bleeding by probing

2: Inflammation in the gum. Bleeding by probing

3: Spontaneous bleeding and tumorigenesis

A relationship between the GI measured in the above manner and the amount of AI-2 measured in (1) is shown in Table 2.

TABLE 2

| GI | AI-2 amount (average, nmol/one (1) tooth) | SE | Dunnett |
|---|---|---|---|
| 0 | 1.03 | 0.28 | — |
| 1 | 1.33 | 0.55 | — |
| 2 | 2.45 | 0.41 | $P < 0.05$ |
| 3 | — | — | — |

As is apparent from Table 2, there is a correlation between the amount of AI-2 in the dental plaque and GI, and the amount of AI-2 contained in the subgingival dental plaque is increased when the gum is inflamed. Therefore, the presence or absence of the onset of periodontal disease can be determined simply and accurately by quantifying the amount of AI-2 in a subject's oral cavity.

(4) Relationship Between Amount of AI-2 in Dental Plaque and Bleeding on Probing (BOP)

A dental probe was inserted into a subject's periodontal pocket, and the presence or absence of bleeding from the periodontal pocket was evaluated on a 4-point scale. Bleeding on Probing (BOP) score evaluation is as follows:

(BOP)
  0: No bleeding
  1: Petechial bleeding
  2: Splinter bleeding
  3: Spontaneous bleeding A relationship between the BOP measured in the above manner and the amount of AI-2 measured in (1) is shown in Table 3.

TABLE 3

| BOP | AI-2 amount (average, nmol/one (1) tooth) | SE | Dunnett |
|---|---|---|---|
| 0 | 1.18 | 0.26 | — |
| 1 | 2.44 | 0.62 | $P < 0.05$ |
| 2 | 2.38 | 0.61 | $P < 0.05$ |
| 3 | — | — | — |

As is apparent from Table 3, there is a correlation between the amount of AI-2 in the dental plaque and BOP. In a subject in which gingival bleeding is caused by probing, the amount of AI-2 contained in subgingival dental plaques is increased. Therefore, the presence or absence of the onset of periodontal disease can be determined simply and accurately by quantifying the amount of AI-2 in a subject's oral cavity.

The above results clinically show a correlation between the amount of AI-2 in the oral cavity and periodontal disease. Therefore, the AI-2 present in the oral cavity can be used for the marker for determining the onset of periodontal disease and the marker for determining the progression stage of periodontal disease.

Example 2

Screening for Improving Agent or Preventive Agent for Periodontosis

A *Vibrio harveyi* BB170 strain (cultured in an AB medium at 30° C. overnight) was used as an AI-2 reporter bacterium and it was 4500-fold diluted with an AB culture medium to prepare a reporter bacterium liquid. A reporter bacterium liquid was mixed with each of the test drugs, which was preincubated at room temperature for 10 minutes, followed by addition of DPD and aerobic shaking culture at 30° C. Four (4) hours later, the photogenesis intensity was measured with the chemiluminescence analyzer (LB940 type, manufactured by Berthold Japan co. ltd.). AI-2 was quantified from the measured photogenesis intensity in the same manner as described in Example 1.

Compound 1: 4-bromo-5-(4-methoxyphenyl)-2(5H)-furanone (manufactured by SIGMA), Compound 2: 3,4-dibromo-5-hydroxy-2(5H)-furanone (manufactured by SIGMA), Compound 3: 4-bromo-5-methoxy-5-(4-methoxyphenyl)-2(5H)-furanone (manufactured by SIGMA), and Compound 4: 4-{[3-bromo-2-(4-methoxyphenyl)-5-oxo-2,5-dihydro-2-furanyl]oxy}benzoate (manufactured by SIGMA) were used as test drugs. As positive controls, three (3) kinds of known compounds as an AI-2 inhibitory compounds, such as Compound 5: 4-hydroxy-2,5-dimethyl-3(2H)-furanone (manufactured by SIGMA), Compound 6: 2-methoxy-2,4-diphenyl-3(2H)-furanone (manufactured by SIGMA), and Compound 7: 2-pentyl-2-cyclopentene-1-one (manufactured by SIGMA) were used (see Bassseler et al., Bacteriol. 179, p. 4043-4045, 1997; Yoshida A. et al., Appl. Environ. Microbial., 71(5), p. 2372-2380, 2005; and Wen Z. T. et al., J. Bacteriol., 189(9), p. 2682-2691, 2004).

The amount of AI-2 was a relative value to the amount of DPD of the control (the amount of AI-2) when one obtained by adding only the DPD without adding the test drugs was used as a control. The results are shown in Table 4.

TABLE 4

| Test Drug | AI-2 amount (relative value) |
|---|---|
| None (Control) | 100 |
| Compound 1 | 29.6 |
| Compound 2 | 0 |
| Compound 3 | 62.5 |
| Compound 4 | 76.0 |
| Compound 5 | 77.0 |
| Compound 6 | 88.9 |
| Compound 7 | 63.4 |

As shown in Table 4, it is found that Compounds 1 to 4 have AI-2 activity inhibitory effect equal to or more than that of the known AI-2 inhibitory compound.

The mandibule of syrian hamsters (three males, 7 weeks old) was extracted under anesthesia and a photograph was taken under the stereoscopic microscope. An evaluation site is the lingual surface of extraction mandibule. The obtained photographs were subjected to image analysis and a vertical distance from the first molar mesial cusp tip to the alveolar tip was measured.

Floss was tied around the left and right mandibular first molar teeth of other syrian hamsters (three males, 7 weeks old). From the next day on, 200 μL of a PBS solution containing 1% DMSO (concentration: 10 μM) of Compound 1 or 2 above was added dropwise to the same tied sites twice a day for two weeks and they were bred.

After the end of breeding, the mandibule was extracted under anesthesia and photographs were taken under the stereoscopic microscope. Taken photomicrographs are shown in FIGS. 1(a) to (c). An evaluation site is the lingual surface of extraction mandibule and the taken photographs were subjected to image analysis. The taken photographs were subjected to image analysis and a vertical distance from the first molar mesial cusp tip to the alveolar tip was measured.

The alveolar bone resorption depth (a value before addition is subtracted from a value after addition for two weeks) was measured from the vertical distance from the first molar mesial cusp tip to the alveolar tip before addition of the test drug and after addition of the test drug for two weeks. The results are shown in Table 5.

TABLE 5

| Test Drug | Alveolar bone resorption depth (mm) | Dunnett |
|---|---|---|
| Control | 2.87 | — |
| Compound 1 | 2.50 | P < 0.01 |
| Compound 2 | 2.62 | P < 0.05 |

FIG. 1 and Table 5 show that absorption of the alveolar bone is suppressed by adding dropwise Compound 1 or 2 having AI-2 activity inhibitory effect to the oral cavity, there is a correlation between the amount of AI-2 present in the oral cavity and periodontal disease, and a compound having AI-2 activity inhibitory effect is effective in preventing and improving (treating) periodontal disease.

Therefore, an improving agent or preventive agent for periodontal disease can be screened by selecting a test drug having AI-2 activity inhibitory effect.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A method of selecting an agent that improves periodontal disease, comprising:
   (a) mixing a bacterium having an autoinducer-2-mediated quorum sensing system and autoinducer-2 in the presence and absence of a test substance;
   (b) measuring the autoinducer-2 activity produced in the presence and absence of said test substance from (a); and
   (c) selecting said test substance as an agent that improves periodontal disease if the autoinducer-2 activity in the presence of said test substance is 29.6% or less of the autoinducer-2 activity in the absence of said test substance.

2. The method of claim 1 wherein said bacterium is *Vibrio harveyi* BB 170.

3. The method of claim 1 wherein said autoinducer-2 is 4,5-dihydroxy-2,3-pentanedione (DPD) or a furanosyl borate diester.

4. The method of claim 1 wherein said bacterium is incubated at room temperature with said test substance before the addition of said autoinducer-2.

5. The method of claim 4 wherein said bacterium, said test substance, and said autoinducer-2 are incubated with aerobic shaking at about 30° C. after the addition of said autoinducer-2.

6. The method of claim 4 wherein the incubation is from 1 to 30 minutes.

7. The method of claim 5 wherein the aerobic shaking is from 2 to 6 hours.

8. The method of claim 1, wherein said periodontal disease is periodontitis.

9. The method of claim 8, wherein said improvement of periodontitis is suppression of the absorption of the alveolar bone.

* * * * *